(12) United States Patent
Munier et al.

(10) Patent No.: US 10,838,077 B2
(45) Date of Patent: Nov. 17, 2020

(54) DEVICE FOR DETERMINING A DEPOSITED DOSE AND ASSOCIATED METHOD

(71) Applicant: Fibermetrix, Strasbourg (FR)

(72) Inventors: Mèlodie Munier, Strasbourg (FR); Till Sohier, Strasbourg (FR); Fayçal Torche, Strasbourg (FR); Fanny Carbillet, Strasbourg (FR)

(73) Assignee: Fibermetrix, Strasbourg (FR)

( * ) Notice: Subject to any disclaimer, the term of this patent is extended or adjusted under 35 U.S.C. 154(b) by 0 days.

(21) Appl. No.: 16/315,835

(22) PCT Filed: Jul. 6, 2017

(86) PCT No.: PCT/FR2017/051847
§ 371 (c)(1),
(2) Date: Jan. 7, 2019

(87) PCT Pub. No.: WO2018/007763
PCT Pub. Date: Jan. 11, 2018

(65) Prior Publication Data
US 2019/0310381 A1    Oct. 10, 2019

(30) Foreign Application Priority Data
Jul. 8, 2016    (FR) ...................... 16 56612

(51) Int. Cl.
*G01T 1/20*    (2006.01)
*G01T 1/02*    (2006.01)
*A61B 6/00*    (2006.01)

(52) U.S. Cl.
CPC ............... *G01T 1/023* (2013.01); *G01T 1/20* (2013.01); *A61B 6/58* (2013.01)

(58) Field of Classification Search
CPC .. G01T 1/02; G01T 1/201; G01T 1/29; G01T 1/20; G01T 1/023; G01T 1/2914; A61N 2005/1087; A61N 5/1048
See application file for complete search history.

(56) References Cited

U.S. PATENT DOCUMENTS 5,233,990 A * 8/1993 Barnea ...................... A61B 6/00
                                                    378/65
5,704,890 A * 1/1998 Bliss .................... A61N 5/1048
                                                    600/1

(Continued)

FOREIGN PATENT DOCUMENTS

EP    0740167 A1    10/1996
EP    0749020 A2    12/1996

(Continued)

OTHER PUBLICATIONS

International Written Opinion for International Application No. PCT/FR2017/051847 dated Sep. 21, 2017, 7 pages.

(Continued)

*Primary Examiner* — Kiho Kim
(74) *Attorney, Agent, or Firm* — TraskBritt

(57) ABSTRACT

A device for determining an ionizing radiation dose deposited by a medical imaging apparatus during a radiological examination of a patient includes at least one measurement probe comprising at least one optical probe defining two exit ends, the optical probe comprising at least one active section made from a scintillator and intended to emit photons under the effect of incident ionizing radiation and at least two transport sections that are placed on either side of the active section and configured to transport the photons emitted by the active section to the exit ends; at least one detection system comprising at least two photodetectors, each photodetector being connected to one respective exit end of the optical probe to receive and count the photons received from (Continued)

the exit end; and at least one processing module configured to determine the deposited dose on the basis of the measurements carried out by the photodetectors.

19 Claims, 6 Drawing Sheets

(56) References Cited

U.S. PATENT DOCUMENTS

| | | | |
|---|---|---|---|
| 5,856,673 A | 1/1999 | Ikegami et al. | |
| 9,339,243 B2* | 5/2016 | Zhang | A61B 6/025 |
| 2007/0181815 A1* | 8/2007 | Ebstein | G01T 1/02 |
| | | | 250/370.11 |
| 2009/0050812 A1* | 2/2009 | Dunleavy | G01T 1/201 |
| | | | 250/368 |
| 2009/0236510 A1* | 9/2009 | Lacroix | G01T 1/02 |
| | | | 250/252.1 |
| 2012/0049084 A1* | 3/2012 | Abenaim | A61B 6/0457 |
| | | | 250/454.11 |
| 2012/0068075 A1* | 3/2012 | Beddar | A61N 5/1048 |
| | | | 250/362 |
| 2012/0205530 A1* | 8/2012 | Beaulieu | G01T 1/201 |
| | | | 250/252.1 |
| 2012/0294419 A1 | 11/2012 | Tesic et al. | |
| 2015/0014547 A1 | 1/2015 | Damm et al. | |
| 2018/0321389 A1* | 11/2018 | Jung | G01T 1/023 |

FOREIGN PATENT DOCUMENTS

| | | |
|---|---|---|
| JP | 2851319 B2 * | 1/1999 |
| JP | 2014-020901 A | 2/2014 |
| WO | 2012/129661 A1 | 10/2012 |

OTHER PUBLICATIONS

International Search Report for International Application No. PCT/FR2017/051847 dated Sep. 21, 2017, 3 pages.

Defez et al., Dosimetry of diagnostic explorations in radiology by the French Society of Medical Physics, No. 30, Dec. 2014, Abstract only.

* cited by examiner

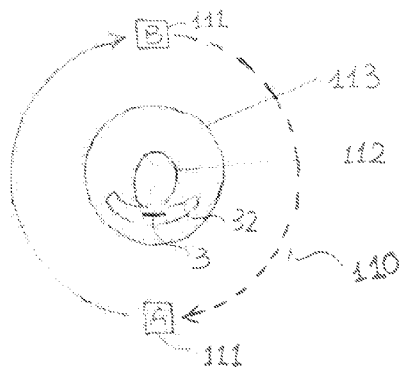
Fig.11a
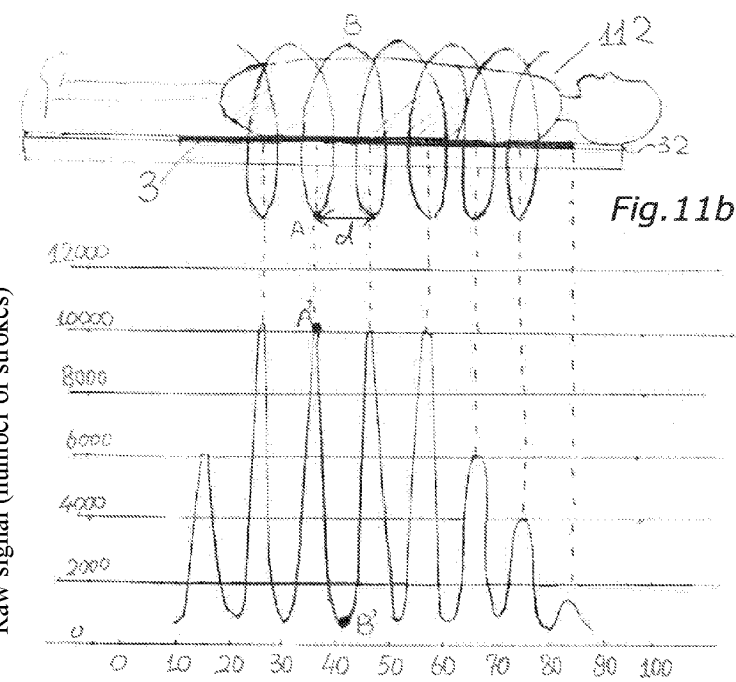
Fig.11b
Fig.11c

DEVICE FOR DETERMINING A DEPOSITED DOSE AND ASSOCIATED METHOD

CROSS-REFERENCE TO RELATED APPLICATIONS

This application is a national phase entry under 35 U.S.C. § 371 of International Patent Application PCT/FR2017/051847, filed Jul. 6, 2017, designating the United States of America and published as International Patent Publication WO 2018/007763 A1 on Jan. 11, 2018, which claims the benefit under Article 8 of the Patent Cooperation Treaty to French Patent Application Serial No. 1656612, filed Jul. 8, 2016.

TECHNICAL FIELD

This disclosure relates to a device for determining a dose deposited under the effect of an irradiation with ionizing radiation generated by an irradiation source of a medical imaging apparatus during a radiological examination of a patient.

BACKGROUND

In view of new rules and regulations, which require minimizing as much as possible the irradiation that a patient is exposed to during a radiological examination, it is important to accurately know, in real time, the irradiation dose deposited during a radiological examination and, in particular, during a Computed Tomographic examination.

It is, therefore, desirable to provide a device for measuring such a dose in a simple and accurate way.

In order to avoid complicating the preparation of the equipment for the radiological examination, it is also important for such a device to be simple to set up.

Some standards now demand scanner manufacturers to include indicators for estimating and adjusting the dose delivered. These indicators correspond to two specific dosimetric quantities, i.e.:

the Computed Tomography Dose Index (IDS or CTDI); and the Product Dose Length (PDL or DLP for Dose Length Product).

Currently, the values of these two indicators are factory-predetermined by the manufacturers of scanners, once and for all, on equivalent adult models (16 cm cylinder for the head and 32 cm cylinder for the chest).

However, since factory calculations are based on these equivalent models, the dose in children and some patients of slight build is underestimated. Indeed, the CTDI increases when the irradiated volume decreases. On the contrary, it is overestimated in the case of patients with above-average build.

In addition, the data (CTDI, PDL) integrated in the scanners during manufacture by the manufacturer is often based on calculation methods or simulations with no possibility of evolution.

It is, therefore, desirable to provide a device making it possible to determine the actual dose received in a customized way, i.e., for each patient and on the basis of actual measurements.

One of the purposes of the present disclosure is to provide a device for the real-time determination of the dose deposited during a radiological examination in a simple and accurate manner.

For this purpose, disclosed herein is a device for determining a deposited dose as mentioned above, comprising:

at least one measurement probe, comprising at least one optical probe defining two exit ends, the optical probe comprising at least one active section made from a scintillator and intended to emit scintillation photons under the effect of incident ionizing radiation and at least two transport sections, that are placed on either side of the active section and configured to transport the scintillation photons emitted by the active section to the two exit ends;

at least one detection system comprising at least two photodetectors, each photodetector being connected to a respective exit end of the optical probe so as to receive and count the scintillation photons received from the exit end; and at least one processing module, configured to determine the deposited dose on the basis of the measurements carried out by the photodetectors.

According to particular characteristics, the determination device comprises one or more of the following characteristics, taken separately or in any technically possible combination(s):

the deposited dose is directly correlated to the amount of photons emitted under the ionizing radiation received by the patient undergoing the radiological examination;

the optical probe is configured such that the active section is exposed to ionizing radiation at the same time as the patient in order to monitor the dose deposited on each part of the patient's body in real time;

the optical probe is U-shaped;

at least two optical probes have common exit ends;

each optical probe has exit ends distinct from the exit ends of the other probe(s), with each exit end being connected to a respective photodetector;

a positioning system is configured for positioning the measurement probe on a table of a medical imaging apparatus, with the positioning system preferably comprising a mat in which the measurement probe is housed;

a receiving box housing the detection system;

receiving box and the measurement probe comprise complementary connectors configured for the releasable connection of the measurement probe to the receiving box;

a plurality of interchangeable measurement probes, with each measurement probe being provided with calibration information specific to the measurement probe;

each measurement probe is provided with an RFID chip containing the calibration information, with the RFID chip being configured to communicate the calibration information to the processing unit when the measurement probe is connected to the receiving box;

wherein the receiving box comprises means for releasable attachment to a table of a medical imaging apparatus, with the table being movably mounted with respect to a body of the medical imaging apparatus so as to move through the irradiation field of the medical imaging apparatus;

a power supply system for the determination device, with the power supply system comprising a rechargeable battery housed in the receiving box and a charging unit housed in a charging base 68 and configured to wirelessly recharge the battery, in particular, by induction;

the charging base comprises removable means for attachment to a stationary part of a medical imaging apparatus, with the table of the medical imaging apparatus being slidably mounted with respect to the stationary part, with the charging unit being configured to charge the battery when the table is in a charging position, wherein, when the receiving box is at a distance from the charging base smaller than or equal to the maximum distance allowing the rechargeable battery to be charged, with the receiving box being advantageously positioned above the charging base in the charging position;

the processing module is configured to calculate a counting rate corresponding to the sum of the scintillation photons counted by the photodetectors and to determine the dose deposited in the active section(s) of the measurement probe by ionizing radiation during the irradiation by multiplying the counting rate by a predetermined calibration factor c;

the determination device is further configured to convert the deposited dose into a global dose specific to the irradiation, for example, by multiplying the determined deposited dose by a predetermined conversion factor f;

the determination device is further configured to determine an average dose delivered during an acquisition covering the entire irradiation length, specific to the irradiation, by dividing the total dose thus determined by the total irradiation length during the radiological examination;

the processing module is so configured as to calculate a dose deposited per revolution of the irradiation source, corresponding to the sum of the scintillation photons counted by the photodetectors during one revolution of the irradiation source;

the determination device is so configured as to determine a dose at the patient's skin;

the determination device further comprises a chart of conversion factors f as a function of the parameters of implementation of the medical imaging apparatus stored in a memory of the determination device, with the processing module being so configured to determine the conversion factor f to be used as a function of the parameters of implementation of the medical imaging apparatus during the radiological examination and the basic rules of radiation-matter interaction;

the determination device is associated with a device for determining the dose in the organs by a Monte Carlo simulation, the doses determined using the determination device and, in particular, the total dose specific to the irradiation and/or the average dose delivered during an acquisition covering the entire irradiation length being provided at the input of the device for determining the dose in the organs.

The disclosure also relates to a method for determining a dose deposited under the effect of irradiation by ionizing radiation during a radiological examination of a patient by means of a determination device as mentioned above, comprising:

the reception by the photodetectors of scintillation photons emitted by the at least one active section under the effect of ionizing radiation and the counting of the scintillation photons; and the determination of the deposited dose from the measurements made by the photodetectors.

According to particular characteristics of the determination method:

the determination step includes:

the calculation using the processing module of a count rate corresponding to the sum of the scintillation photons counted by the photodetectors; and determining the deposited dose specific to the irradiation by multiplying the counting rate by a predetermined calibration factor c.

the determination step further comprises converting the deposited dose into a total dose specific to the irradiation, for example, by multiplying the deposited dose determined by a predetermined conversion factor f.

the determination step further includes the determination of an average dose delivered during an acquisition covering the entire irradiation length, specific to the irradiation, by dividing the total dose thus determined by the total irradiation length during the radiological examination.

the determination step further comprises calculating a deposited dose per revolution of the irradiation source, corresponding to the sum of the scintillation photons counted by the photodetectors during one revolution of the irradiation source.

BRIEF DESCRIPTION OF THE DRAWINGS

The characteristics and advantages of the disclosure will appear upon reading the following description, given only by way of a non-restrictive example while referring to the accompanying drawings, wherein:

FIG. 11a is a schematic front view of the scanner;

FIG. 11b is a schematic side view of the scanner; and

FIG. 11c is a curve of the counting rate obtained from the scanner in FIGS. 11a and 11b.

DETAILED DESCRIPTION

Figure 1:
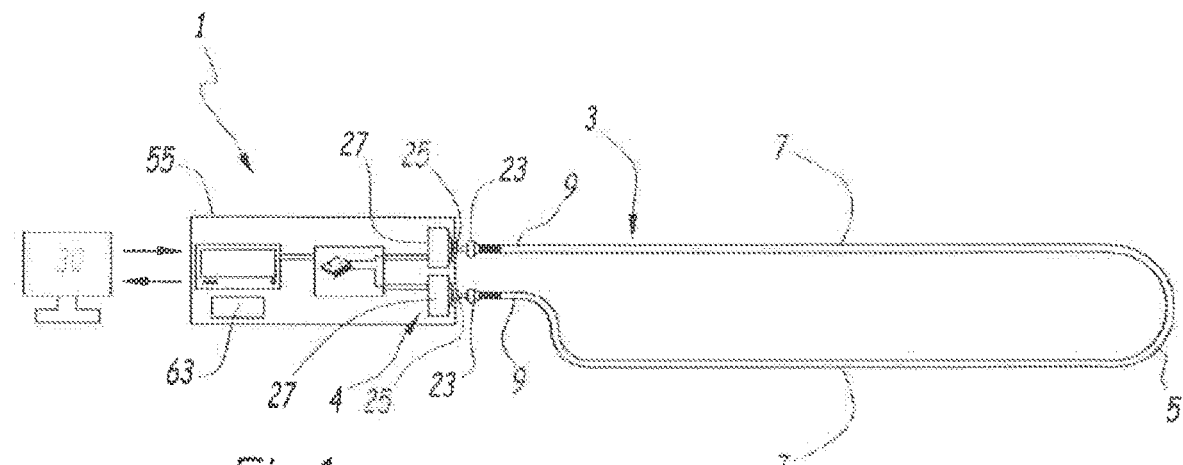
FIG. 1 is a schematic view of a device for determining a dose according to the disclosure.

FIG. 1 schematically shows a device 1 for determining a deposited dose according to the disclosure.

This determination device 1 is intended to be integrated in a medical imaging apparatus comprising an ionizing radiation source in order to measure the dose deposited during a medical imaging examination.

The medical imaging apparatus is advantageously a scanner. In particular, such a scanner comprises a body comprising an ionizing radiation source, and specifically an X-ray tube and a table intended for receiving the patient and slidably mounted through the scanner body. Typically, the body is ring-shaped. For example, the scanner also comprises a headrest intended to be positioned on the scanner table at one end of the table, so that the patient's head can be received and immobilized thereon.

The medical imaging apparatus is, in particular, a scanner that emits medical X-rays.

Preferably, the ionizing radiation has an energy ranging from 10 keV to 250 keV.

As shown in FIG. 1, the determination device 1 comprises a measurement probe 3 intended for receiving an ionizing radiation emitted from the ionizing radiation source.

The measurement probe 3 includes at least one optical probe folded back in a U-shape. In the example shown, the optical probe consists of two sections 7 that are substantially parallel to each other, connected to each other by a section in the shape of an elbow 5. The ends 9 of the optical probe are positioned substantially opposite each other. They form the exit ends of the measurement probe 3.

In the example shown in FIG. 1, the measurement probe 3 includes a single optical probe. The ends 9 of this optical probe form the only two exit ends of the measurement probe 3. In this example, the determination device includes exactly two photodetectors 27, each respectively positioned at one of the exit ends of the measurement probe 3.

More specifically, the optical probe includes at least one active section 11 (FIG. 2) that includes a scintillator.

The active section 11 is intended to emit scintillation photons under the effect of the incident ionizing radiation.

The scintillator is, in particular, an organic or inorganic scintillator. For example, the active section 11 is a sparkling plastic optical fiber. The active section 11 forms a U-shaped section of the optical probe. It consists of a sparkling optical fiber.

The length of the active section 11 is chosen according to the length of the area irradiated by the incident ionizing radiation so as to extend over at least the entire length of the irradiated area.

For example, the probe of the active section 11 has a length between 10 cm and 2 m.

In particular, in the case of an attempt to determine the dose deposited within the scope of a radiological examination carried out on the patient's body, the measurement probe 3 shall comprise at least one active section 11, the length of which shall be chosen in such a way that the measurement probe 3 extends over at least the entire length of the patient's body, while taking into account the variability in patients' sizes and the patients' positioning on the table.

In an alternative solution, when attempting to determine the dose deposited as part of a radiological examination of the patient's skull, the measurement probe 3 includes at least one active section 11 the length of which is chosen such that the measurement probe 3 extends at least over the entire length of the patient's skull, while taking into account the variability of the patients' skull sizes and the patients' positioning on the table.

The optical probe also includes at least two transport sections 13, arranged on either side of the active section 11, for transporting the scintillation photons emitted by the active section 11 to the exit ends 9 of the measurement probe 3. In the example shown in FIG. 1, each transport section 13 is a segment of the U-shaped optical probe.

The transport sections 13 are made of a non-scintillating material when irradiated by ionizing radiation. They are made of plastic or silica.

In particular, each transport section 13 comprises an optical fiber, which will be called a transport optical fiber in the following description.

Figure 2:
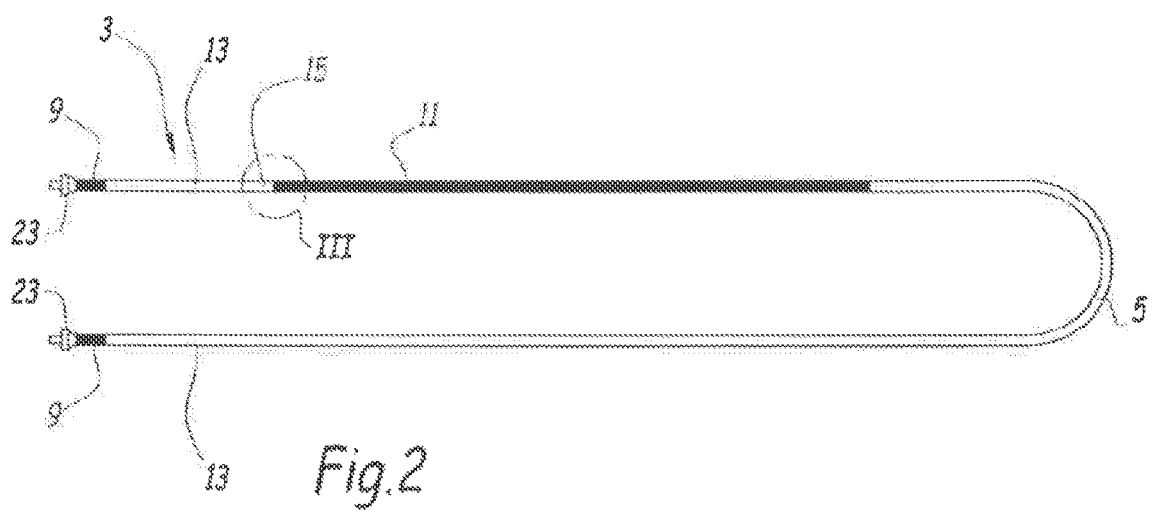
FIG. 2 is a schematic view of a measurement probe of the device of FIG. 1.

In the example shown in FIG. 2, wherein the measurement probe 3 includes a single active section 11, each transport optical fiber 13 is connected to the active section 11 by a first end 15, whereas its second end forms an exit end 9 of the measurement probe 3.

The length of each transport optical fiber 13 is chosen according to the length and location of the active section 11 relative to the location provided for the exit ends 9 of the measurement probe 3.

Preferably, the transport optical fibers 13 are attached to the scintillating optical fiber forming the active section 11 by an optical junction 17. Such junction is shown in greater detail in FIG. 3. It is adapted to transmit the scintillation photons, substantially without any loss, from the scintillating optical fiber of active section 11 to the corresponding transport optical fiber 13. For example, the optical junction 17 is formed by gluing the scintillating optical fiber 11 onto the transport optical fiber 13 using a suitable adhesive.

Figure 3:
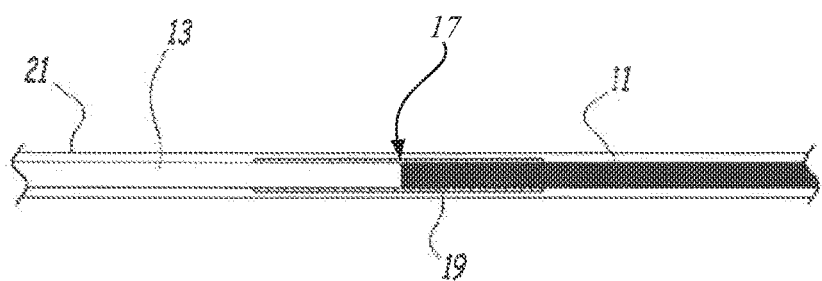
FIG. 3 is a schematic view of a detail from FIG. 2.
Figure 4:
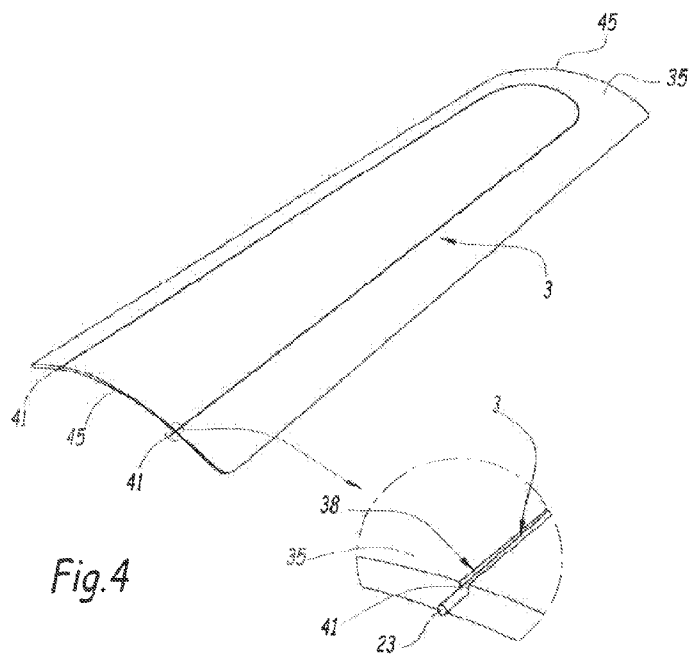
FIG. 4 is a view of the positioning mat integrating the measurement probe of FIG. 1.

Advantageously, and as shown in FIG. 3, at the optical junction 17, the transport optical fiber 13 and the scintillating optical fiber 11 are surrounded by a protective sleeve 19. Such a protective sleeve 19 mechanically reinforces the junction area between the scintillating optical fiber 11 and the transport optical fiber 13.

Advantageously, the measurement probe 3 is surrounded by an opaque sheath 21. Such a sheath 21 ensures that only the scintillation photons emitted by the active section 11 under the effect of the incident ionizing radiation will be transmitted to the ends 9 of the measurement probe 3.

In the embodiment of the disclosure shown in FIG. 3, the protective sleeve 19 is positioned inside the sheath 21. However, as an alternative solution, it could also be positioned outside the sheath 21, at the optical junction 17 between the scintillating optical fiber 11 and the transport optical fiber 13.

According to one embodiment, at least part of the measurement probe 3 and, in particular, the active section 11, is coated with an opacifying paint to improve the opacity of the measurement probe 3 in an ambient light.

According to another embodiment, at least part of the measurement probe 3 and, in particular, the active section 11 thereof, is coated with a thermoplastic sheath using an extrusion process.

As shown in FIGS. 1 and 2, each end 9 of the measurement probe 3 is provided with an output connector 23 so configured as to be engaged into a corresponding input connector 25 of a detection system 4.

The detection system 4 comprises at least two photodetectors 27, with each photodetector 27 being connected to a respective exit end 9 of the measurement probe 3 so as to receive and count the scintillation photons arriving at the exit end 9. In particular, each photodetector 27 is connected to a corresponding exit end 9 of the measurement probe 3 by engaging the corresponding output/input connectors 23, 25 of the measurement probe 3 and the detection system 4.

Each photodetector 27 comprises, for example, a photomultiplier tube, a silicon photomultiplier (known as SiPM), an avalanche photodiode (ADP) or a charge-coupled photodetector, for example, a CCD sensor.

Each photodetector 27 includes its own scintillation photon receiving cell, spaced from the receiving cell of the other photodetector 27.

Each photodetector 27 is connected, within the detection system 4, to a discriminator set to a predetermined detection threshold. The discriminator is so configured as to eliminate the signals measured by the photodetector 27 that have an amplitude below the predetermined detection threshold. The discriminator is so configured as to identify the signals measured by the photodetector 27 with an amplitude above the predetermined threshold upon receipt of at least one scintillation photon.

The detection threshold depends on the measurement probe 3 used and the efficiency of the photodetectors 27. It is preferably higher than the noise level associated with the determination device 1 and mainly including electronic noise from the photodetectors. The detection threshold is chosen so as to enable the reception of a scintillation photon produced by the scintillator to be measured.

Each photodetector 27 is connected to its own discriminator.

At its exit, each photodetector 27 is so configured as to emit a signal, the amplitude of which is proportional to the total number of scintillation photons counted. An amplitude processing of this signal is possible to determine the number of scintillation photons counted.

The determination device 1 also includes a processing module 30 so configured as to calculate the dose deposited in the active section(s) 11 of the measurement probe 3 during the radiological examination from the measurements carried out by the photodetectors 27 and, more particularly, the measured counting rate.

The dose deposited in the active section(s) 11 is expressed in mGy.

In particular, as an example, the processing module 30 is configured so as to calculate the sum of the scintillation photons counted by each of the photodetectors 27. This amount will be referred to as the counting rate in the following description.

FIG. 11 is a curve showing the counting rate thus determined as a function of the z-position of irradiation, i.e., according to the patient's length or the axis of the spiral followed by the medical imaging apparatus.

The processing module 30 is more specifically configured so as to deduce the dose deposited in the active section(s) 11 of the measurement probe 3 by the ionizing radiation by multiplying the counting rate by a predetermined calibration factor c. The calibration factor c is delivered by a calibration laboratory and is obtained by calibrating the processing module 30 under specific irradiation conditions and with dedicated beam qualities.

Advantageously, the calibration factor c is stored in a memory of the determination device 1.

For example, the processing module 30 includes a central processing unit adapted to run the applications required for operation of the determination device 1. For this purpose, the central processing unit comprises a processor and one or more memory device(s). The processor is suitable for running applications contained in the memory device(s), such as an operating system, which enables a computer system to operate in a conventional way. The memory device contains different memory areas containing applications intended to be executed by the processor.

In an advantageous embodiment, the processing module 30 is integrated in a computer remote from the detection system. In this case, the output signal of the detection system 4 is transmitted to the processing module 30 by any suitable transmission mode, including USB, WiFi, Ethernet, for example, via an RJ45 connector or Bluetooth. For example, the remote computer is a desktop or laptop computer, a smartphone or a tablet.

Figure 6:
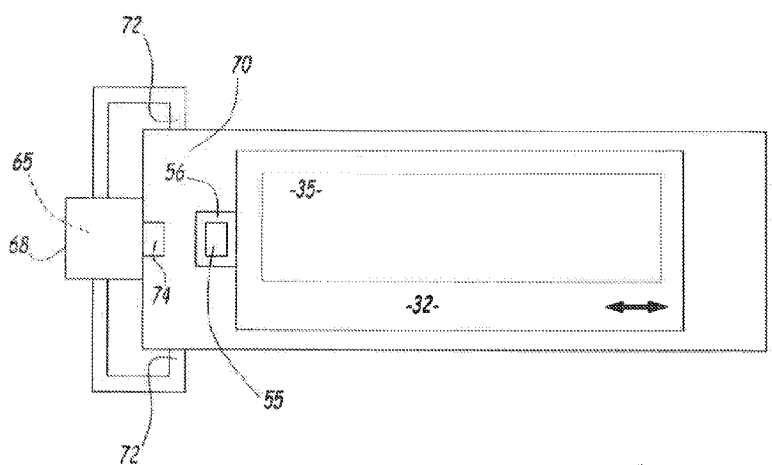
FIG. 6 is a schematic top view of the dose determination device installed on a scanner table.

As shown in FIG. 6, the measurement probe 3 is advantageously designed to be positioned on a table 32 of a medical imaging apparatus and, in particular, a scanner, especially an X-ray scanner.

It is advantageously placed under the patient and, in particular, in direct contact with the patient. In an alternative solution, it is placed on the patient and, in particular, in direct contact with the patient. When the probe is placed in direct contact with the patient, on or under the patient, the dose measured by means of the determination device 1 corresponds to the skin dose.

According to one option, the determination device 1 includes a system for positioning the measurement probe 3 relative to a support. The support is advantageously a table 32 of a medical imaging apparatus, and preferably a table of a scanner.

Preferably, the positioning system includes a positioning mat 35, in which the measurement probe 3 is integrated.

The positioning mat 35 is made of a material with the lowest possible density, preferably equal to the density of water and, therefore, advantageously of about 1 g/cm$^3$.

It is preferably flexible so that it can be adapted to the shape of the support. For example, the positioning mat 35 is made of a textile material or very low-density foam.

Advantageously, the positioning mat 35 is thin. It has, for example, a thickness of 1 cm or less.

In particular, the positioning mat 35 defines, in its lower portion, a housing 38, intended to receive the measurement probe 3. The housing 38 has a shape matching that of the measurement probe 3 in the operating configuration. For example, the housing 38 is U-shaped.

Thus, the position of the measurement probe 3, as well as its geometry in the operating configuration, are set relative to the positioning mat 35.

For example, the housing 38 extends over at least 80% of the length of the positioning mat 35, and preferably over at least 90% of the length of the positioning mat 35.

The positioning mat 35 has a predetermined length relative to the length of the table 32 of the medical imaging apparatus and, more particularly, the scanner. In particular, the positioning mat 35 has a length approximately equal to the length of the table to be inserted into the scanner ring.

For example, the positioning mat 35 has a length of approximately 1.80 m.

In the embodiment shown, the measurement probe 3 is completely included in the one-piece positioning mat 35.

In an alternative solution, the positioning mat 35 may include a first portion, intended to extend at the patient's body and a second portion intended to extend at the patient's head. In this alternative solution, the measurement probe 3 extends over these two mat portions.

Advantageously, the measurement probe 3 is attached in the housing 38 by snap-fitting. For example, the snap-fitting is achieved by means of suitable clips placed in the housing 38. In an alternative solution, the housing 38 is provided with a flange extending inwardly from the edge of the housing 38 so as to allow the measurement probe 3 to be placed in the housing 38 but to prevent its unintentional removal from the housing 38.

The housing 38 has at one end 41 at least one opening allowing the passage of the output connectors 23 of the measurement probe 3. The output connectors 23 of the measurement probe 3 project outside the positioning mat 35 at one of its longitudinal ends 45, particularly at the same longitudinal end 45 of the positioning mat 35. Longitudinal end means one end along the length of the positioning mat 35.

Such a positioning mat 35 is advantageous. Indeed, this positioning mat 35 facilitates the positioning of the measurement probe 3 on the support and, in particular, on the table of the medical imaging apparatus. As a matter of fact, the configuration of the measurement probe 3 is fixed as compared to the table positioning mat 35, which is advantageous in that the measurement probe 3 is flexible and could, therefore, adopt other configurations when it is isolated.

In the case where the positioning mat 35 has dimensions identical to those of a predetermined area of the table 32, it is sufficient to position the positioning mat 35 so that it coincides exactly with the area of the table 32. The measurement probe 3 is then automatically positioned correctly relative to the support and, therefore, to the table.

The positioning mat 35 also protects the measurement probe 3.

The positioning mat 35 is, according to one embodiment, positioned on the scanner table and covered by the mattress usually covering the scanner table, with the mattress being intended to receive the patient during the radiological examination. For example, it also extends under the headrest of the scanner table. In an alternative solution, it is placed on the headrest of the scanner table and, for example, under a padded cushion whereon the patient's head will rest.

According to an alternative embodiment, not shown, the support is formed by the headrest of the medical imaging apparatus. In this case, the positioning mat 35 is intended to be placed on the headrest, and possibly covered by a padded cushion.

In another alternative solution, the support is formed by the patient's body and the positioning mat 35 is designed to be placed on the patient's body, like a blanket.

In an advantageous embodiment, the processing module 30 is so configured as to determine other dosimetric quantities for the radiological examination from the measurements carried out by the photodetectors 27.

According to this embodiment, the medical imaging apparatus is a scanner.

In particular, the processing module 30 is so configured as to calculate, for each radiological examination, the overall dose received by the patient, called DG in the following description, specific to the examination, from the determined counting rate. The DG is expressed in mGy.cm.

For this purpose, for example, the processing module 30 is so configured as to convert the deposited dose determined by the detection system 4 during the irradiation period in order to obtain the DG specific to the irradiation.

In particular, when the determination device 1 is used during the scan examination of a patient, the DG thus determined corresponds to the Patient Specific Dose Length Product (DLP) and the radiological examination performed.

According to a first calculation method, the processing module 30 is so configured as to convert the determined deposited dose to DG by multiplying the determined deposited dose by a predetermined conversion factor f.

The predetermined conversion factor f is advantageously taken by the processing module 30 from a conversion factor chart f stored in the memory of the determination device 1 according to scanner implementation parameters and basic radiation-matter interaction rules.

These implementation parameters are parameters that may influence the value of the DG. They include, for example, irradiation geometry and acquisition parameters.

In particular, the chart includes conversion factors f determined for different values of these scanner implementation parameters. Thus, the processing module 30 is so configured as to extract from the chart the conversion factor adapted according to the values taken by the implementation parameters during the computed tomographic examination considered.

According to one embodiment, if several acquisitions are made on the same anatomical area during the radiological examination, the DGs determined for each acquisition are added. If the acquisitions concern different anatomical areas, the DGs are indicated separately for each of the areas concerned.

The processing module 30 is advantageously so configured as to exchange data with a hospital computer network and, in particular, to obtain the implementation parameters from the computer network.

The disclosure also relates to a method for determining at least one conversion factor f.

Figure 5:
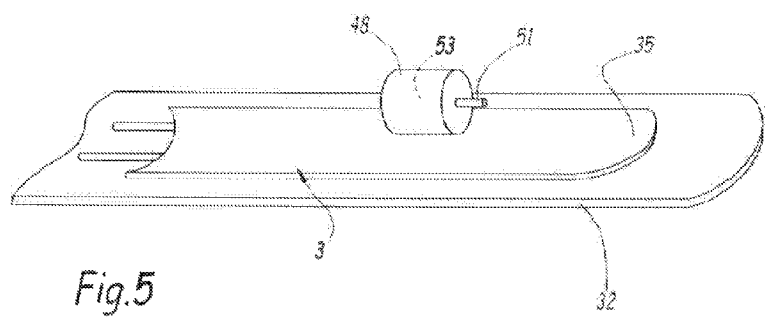
FIG. 5 is a schematic view of a facility for the calibration of the determination device of the disclosure.

An exemplary implementation of such method is shown in FIG. 5.

The method for determining the conversion factor f comprises, in the absence of a patient, for each considered combination of values of implementation parameters:

the positioning of the measurement probe 3 on the table 32 of the scanner;

the positioning of a cylindrical phantom 48 made of polymethyl methacrylate (PMMA) on the table of the medical imaging apparatus;

the irradiation of the phantom 48 for a predetermined irradiation time;

the determination, using the determination device 1 according to the disclosure, of a dose deposited in the active section(s) 11 of the measurement probe 3 for a predetermined irradiation time;

the determination of a reference CTDIvoL under the same conditions; and the determination of the conversion factor f by dividing the reference CTDIvoL by the deposited dose determined under the same conditions.

The conversion factor f has no unit. It is specific to the measurement probe 3 used. The reference CTDIvoL is determined using a conventional method.

For example, in order to determine the reference CTDIvoL, the Cw weighted scanning kerma index (ICRU 74: weighted CT air kerma index), referred to as CTDIW in the following, is measured using a 10 cm long pencil ionization chamber 51 arranged successively in five chambers formed in the cylindrical phantom 48 in PMMA. More specifically, these housings include: a central housing 53 and four peripheral housings, spaced angularly evenly according to the periphery of the phantom 48. In particular, the peripheral housings are arranged 1 cm away from the surface of the phantom 48. Only the central housing 53 is illustrated in FIG. 5. Five separate dose measurements are thus obtained.

The CTDIW is obtained by applying the following formula:

$$CTDI_w = 1/3 \times C_c + 2/3 \times C_p$$

where Cc is the result of the measurement in the central housing 53 and Cp is the arithmetic mean of the four measurement results in the peripheral housing.

The reference CTDIVOL is obtained by dividing the CTDIW by the pitch of the spiral p.

The pitch p of the spiral or "pitch factor" corresponds to the displacement of the scanner bed during a revolution of the irradiation source divided by the width of the irradiation window.

In this method for determining the conversion factor f, the pitch p is equal to 1. As a matter of fact, the scanner operates in axial or sequential mode for the implementation of this method, and not in helical mode.

This method for determining the reference CTDIVOL is conventional. It is described in particular in paragraph 1.3.2, on pages 15 and 16 of the document entitled "Dosimetry of diagnostic explorations in radiology" by the French Society of Medical Physics (December 2014 version).

For example, the method for determining the conversion factor f comprises the determination of a first series of conversion factors f, intended for use in an exocranial computed tomographic examination performed on the patient's body, using, in the method described above, a cylindrical phantom 48 having a diameter characteristic of the body of an average patient, in particular, 32 cm in diameter.

For example, the method for determining the conversion factor f includes the determination of a second series of conversion factors, intended for use in a computed tomographic examination performed on the patient's skull only, using, in the method described above, a cylindrical phantom 48 with a diameter characteristic of the skull of an average patient, in particular, 16 cm in diameter.

According to a second method of calculation of the DG, the processing module 30 is so configured as to convert the dose deposited in the active section(s) 11 of the measurement probe 3 determined by the processing module 30 into a DG, not by means of a conversion factor f, but from an expression taking into account patient-specific parameters and, for example, actual patient's dimensions. Thus, the deposited dose is directly correlated to the amount of photons emitted under the effect of the ionizing radiation received by the patient undergoing the radiological examination. This calculation method avoids referring to simulation methods on equivalent models from phantoms modelling patients and makes it possible to accurately know in real time the irradiation dose deposited during a radiological examination.

As explained in greater detail below in an example, these specific parameters are, for example, deduced from the dose measurement performed by means of the determination device 1 or are obtained by taking into account additional information from, for example, the scanner, such as images or metadata.

For example, this expression is deduced from an equation representing the energy loss of photons X in an homogeneous or non-homogeneous organic medium of the $K=K_0 exp(-px)$ type, where x is the thickness through which photons X pass and p represents the total attenuation coefficient of the medium traversed. K represents the dose received by a patient after the photons pass through a thickness x.

When the total attenuation coefficient p is pre-established, the dimensions of the patient and, in particular, the transverse, e.g., antero-posterior and lateral dimensions, are determined, for example, from the deposited dose profiles measured using the determination device 1 for that patient.

As an alternative solution, the patient's dimensions can also be extracted from the DICOM images generated by the scanner.

Information on the patient's dimensions is used, in particular, to determine the thickness through which the photons pass in order to apply the above expression.

When the total thickness of the patient is known, the skin dose, the entry dose and the dose at different depths inside the patient are, for example, also obtained from the deposited dose profiles measured using the determination device 1 for this patient. This information is used, for example, to determine the attenuation coefficient used in the above expression.

The total DG dose is determined from the doses received by a patient at different depths.

Advantageously, the processing module 30 is also so configured as to determine, for each radiological examination, with the average dose delivered during an acquisition covering the entire irradiation length, called DM in the following text, specific to the radiological examination. The DM is expressed in mGy. In the case of a computer tomographic examination, it corresponds to the patient-specific volume scan dose index (CTDIvoL) and the computer tomographic examination performed.

For this purpose, the processing module 30 is so configured as to divide the DG previously determined by the total length of irradiation during the radiological examination.

The total irradiation length is the total length of the patient's body irradiated during the radiological examination.

As an option, the processing module 30 is also so configured as to determine a patient's skin dose specific to this irradiation.

FIG. 11a is a front schematic view of a scanner, while FIG. 11b is a side view thereof. FIG. 11c shows the measurement result (dose profile) obtained in the examination configuration defined in FIGS. 11a and 11b.

FIG. 11a schematically illustrates a scanner 110 according to the disclosure. The patient 112 is lying on the table 32, which contains the measurement probe 3. The patient 112 and the table 32 are housed in the space delimited by the wall of the scanner ring 113. The irradiation source 111 makes a rotational movement around the patient 112 following the path indicated by the arrows.

Revolution means a 360° rotation of the irradiation source 111 and, in particular, the X-ray tube. During one revolution, because of the translational displacement of the table 32 during the examination, the irradiation source 111 follows a helical path while moving in a translational displacement by a distance d from the patient, as shown in FIG. 11b. The processing module 30 is so configured as to evaluate, for each scanner revolution, the DGj and the associated DMj, where j corresponds to the $j^{th}$ rotation of the scanner. The DGj and DMj are determined from the doses received by a patient at different depths at the $j^{th}$ rotation of the scanner.

Thus, in helical mode, the DGj and DMj, respectively, correspond to the total dose received by the patient DG and the average dose DM delivered into the patient's jth section or cylinder, the length of which is equal to d, DMj=DGj/d.

The processing module 30 is so configured as to construct a curve representing the counting rate as a function of time and, therefore, indirectly as a function of the irradiation Z-position, i.e., according to the length of the patient or according to the axis of the spiral followed by the medical imaging apparatus. An example of such a dose profile curve, expressed as a function of the z-position of irradiation, is shown in FIG. 11c.

This curve is in the form of a curve with maxima, resulting from the irradiation of the measurement probe 3 when the measurement probe 3 is between the irradiation source 111 and the patient 112 and minima, resulting from the irradiation of the measurement probe 3 when the patient 112 is between the irradiation source 111 and the measurement probe 3.

In order to discuss the details of the curve, the movement of the irradiation source 111 in the direction indicated by the continuous arrow from point A to point B in FIG. 11a is considered. When the irradiation source 111 is located behind the patient's spine 112 in the position of point A in FIGS. 11a and 11b, the measurement probe 3 is exposed directly under the radiation from the source, which leads to the maximum amplitude A' of the curve shown in FIG. 11c.

Whereas, when the irradiation source 111 is located in front of the patient 112 in the position of point B in FIGS. 11a and 11b, the measurement probe 3 is sheltered by the patient's body 112, which leads to the minimum amplitude B' of the curve presented in FIG. 11c. Thus, the irradiation source makes a complete revolution around the patient between two successive minima or between two successive maxima of the output signal.

Further to the modulation of the intensity of the irradiation source according to the thickness or density of the patient's body, the amplitudes of the maxima of the curve vary in FIG. 11c. When the scanner is on the abdomen, which part of the patient has a large and dense thickness, the intensity of the irradiation source is high, leading to the amplitudes of the higher maxima, and corresponding to the peaks between 20 mm and 60 mm in the Z-position in FIG. 11c. When the scanner is on the chest containing the lungs, this part of the patient has a thin and sparse thickness. The intensity of the irradiation source is thus reduced, which results in lower maximum amplitudes, and corresponds to peaks between 60 mm and 80 mm of the Z-position in FIG. 11c.

Thus, this method makes it possible to determine the dose actually received by the patient in a customized way, i.e., for each patient and from actual measurements without referring to a phantom.

In particular, the processing module 30 is so configured as to determine the deposited dose per scanner revolution by implementing the following steps:
  determining the total number of photons counted between two successive minima of the curve representing the counting rate as a function of time or between two successive maxima of the curve; then
  determining the deposited dose per scanner revolution by multiplying the total number of photons thus counted by the predetermined calibration factor c described above.

The processing module 30 is also advantageously so configured as to:
  convert the deposited dose thus determined per scanner revolution into DG; per scanner revolution, for example by multiplying the deposited dose by the predetermined conversion factor f described above or using an expression taking into account the patient's dimensions as described above.

The total number of photons counted for a scanner revolution is obtained by integrating the curve between two successive minima or between two successive maxima.

As an option, the processing module 30 is also so configured as to determine a DM per scanner revolution by dividing this DG by the irradiation length for a scanner revolution.

The irradiation length for a scanner revolution corresponds in particular to the distance of movement of the scanner bed during a scanner revolution.

Determining a DG and a DM makes it possible to take into account the operation of the scanners in current modulation and RX tube voltage mode, since the DM is not constant during the acquisition.

As an option, the determination device 1 is associated with an organ dose-determination device by Monte Carlo simulation, with the doses determined using the determination device 1, and, in particular, the DG and DM being provided at the input of the organ dose-determination device.

Such devices for determining the organ's dose by Monte Carlo simulation are known and will not be described in greater detail herein.

This option provides a more accurate assessment of the organ dose. As a matter of fact, these simulations are currently based on dose parameters obtained by phantom simulation and not on dose measurements carried out on each patient in clinical routine.

Advantageously, the detection system 4 is housed in a receiving box 55. This receiving box 55 comprises the input connectors 25 intended to receive output connectors 23 of the measurement probe 3. These input connectors 25 are connected, inside the receiving box 55, to the inlets of the two photodetectors 27.

According to one embodiment, the processing module 30 is integrated in the receiving box 55.

In the embodiment wherein the processing module 30 is integrated in a remote computer, the receiving box 55 advantageously includes at least one communication module configured to enable the transmission of the output signal from the detection system 4 to the processing module 30 and, in particular, a USB port, an RJ45 connector, a Bluetooth communication module, or a Wi-Fi adapter.

Figure 7:
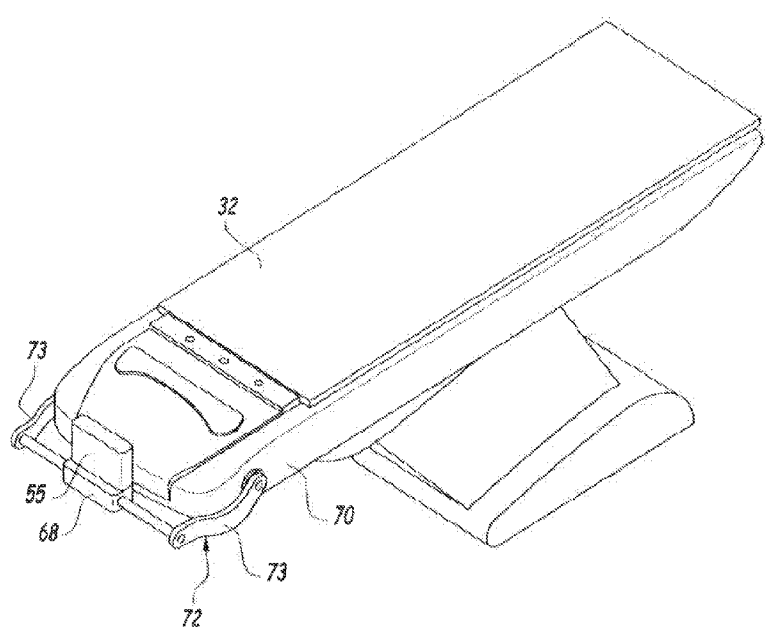
FIG. 7 is a perspective representation of a scanner table equipped with a part of the device according to the disclosure, with the receiving box being in the recharging position above the recharging base.

As shown in FIGS. 6 and 7, the receiving box 55 is intended to be placed outside the irradiation field, for example, at one end of the table 32 of the medical imaging apparatus that is outside the irradiation field of the device over the entire travel of the table 32 through the body of the medical imaging apparatus.

Advantageously, the receiving box 55 is equipped with removable attachment means on a support and, in particular, on table 32.

For example, these removable attachment means comprise means for gluing the receiving box 55 onto the support, with the gluing means allowing the receiving box 55 to be repositioned relative to the support.

For example, the gluing means are associated with a support plate 56 integral with the receiving box 55, with the support plate 56 having a shape adapted to a given model of computed tomography table.

According to one embodiment, the removable attachment means are chosen in such a way that they can be adapted to attachment areas on the support of variable dimensions so that the receiving box 55 can be reliably attached to various supports.

The determination device 1 also includes a power supply system for the receiving box 55.

This power supply system includes a rechargeable battery 63, shown schematically in FIG. 1, designed to provide the power required for operating the detection system 4, particularly during a radiological examination. Advantageously, the rechargeable battery 63 is housed in the receiving box 55.

Advantageously, the power supply system also includes a charging unit 65, so configured as to recharge the battery 63. In particular, the charging unit 65 is housed in a charging base 68 as shown in FIGS. 6 and 7.

For example, the charging unit 65 is so configured as to wirelessly charge the battery 63.

In particular, it is so configured as to recharge the battery 63 by induction. In this case, the charging unit 65 includes, for example, a primary coil, whereas the receiving box 55 includes a secondary coil, connected to the battery 63.

However, any other wired or wireless charging mode can be used as an alternative for charging the battery 63.

Wireless recharging is advantageous because it avoids the presence of wires connected to the moving part of the table and, therefore, the problems resulting from the winding or unwinding of these wires when moving the table 32.

The charging base 68 is preferably attached to a stationary part 70 of the medical imaging apparatus and, more particularly, to a stationary part 70 slidably receiving the table 32 of the medical imaging apparatus. In particular, it is attached to the stationary part 70 by removable attachment means 72.

For example, and as shown in FIGS. 6 and 7, these removable attachment means 72 include jaws 73 so configured as to rest by pressure on the stationary part 70.

As an option, the removable attachment means 72 also include a support tab 74 on the support, so configured as to prevent the charging base 68 from tilting relative to the support in a direction perpendicular to the direction of the pressure exerted by the jaws 73.

Advantageously, the removable attachment means 72 are chosen so as to adapt to attachment zones on the stationary part 70 of variable dimensions so as to enable a reliable attachment of the charging base 68 on various supports.

The receiving box 55 and the charging base 68 are advantageously arranged in such a way that, in at least one position of the table 32 of the medical imaging apparatus, referred to as the charging position, the receiving box 55 is located at a distance from the charging base 68 smaller than or equal to the maximum distance allowing charging.

In particular, in the charging position, the receiving box 55 is located opposite the charging base 68 and, in particular, above the latter.

As an alternative solution or as an option, the battery 63 can be charged by plugging a corresponding connector from the receiving box 55 into the main supply.

Figure 8:
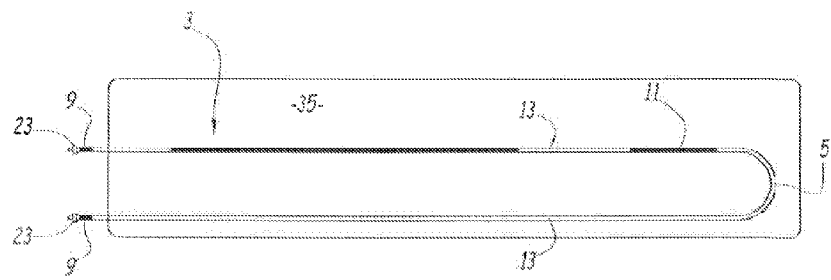
FIGS. 8 to 10 are schematic representations of measurement probes according to alternative embodiments.
Figure 9:
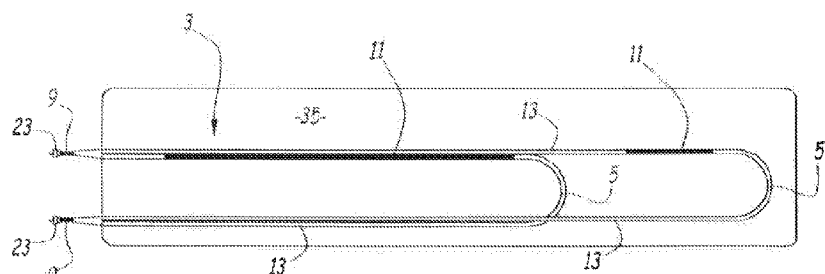
Figure 10:
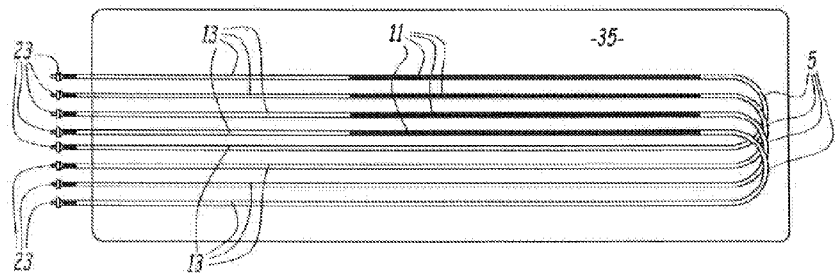

In the embodiment shown in FIG. 2, the measurement probe 3 has a single active section 11. FIGS. 8 to 10 illustrate measurement probes 3 according to alternative embodiments.

According to a first alternative embodiment of the determination device 1 shown in FIG. 8, the measurement probe 3 has two active sections 11, connected to each other by a transport section 13. Each active section 11 is intended to extend to a respective section of the patient's body examined during the radiological examination for which a dose indication is desired using the determination device 1.

For example, one of the active sections 11 is intended to be located under the patient's body, except for the skull, while the other active section 11 is intended to be located under the patient's skull. It is thus possible, using the same measurement probe 3, to determine the dose deposited during the irradiation of various areas of the body, except for the skull, on the one hand, and of the skull on the other hand.

The two active sections 11 have, in the example shown, different lengths, adapted to the section of the patient's body for which it is intended.

According to a second alternative embodiment illustrated in FIG. 9, the measurement probe 3 includes two U-shaped optical probes, each of which includes an active section 11, the length and position of which are adapted to the particular area to be irradiated.

For example, a first U-shaped optical probe includes an active section 11 to be located under the patient's body, except for the skull, while the other optical probe includes an active section 11 to be located under the patient's skull. In the example shown, the ends of the two U-shaped optical probes are connected together in pairs and lead to a common output connector 23.

The processing module 30 is so configured as to determine, at each sampling time of the photodetectors 27, the irradiation position z of the optical probe at which the scintillation photons received by photodetectors 27 were emitted at that sampling time using a predefined calibration line according to the output signals of the photodetectors 27.

This calibration line is stored in the memory of the determination device 1.

Advantageously, the calibration line is a line with the following equation:

$$f(z) = az + b, \text{ with:}$$

z is the irradiation position along the axis z, the axis z corresponding to the translation axis of the table 32, f(z) is the quotient of the output signals of the two photodetectors 27 or alternatively the quotient of the difference of these signals on their sum;

a and b are predetermined calibration constants.

Thus, the processing module is configured to calculate, at each sampling time, the quotient f(z) and to deduce therefrom a corresponding position z.

Thus, the processing module 30 is so configured as to associate a z position with each irradiation by the scanner.

The processing module 30 is able to determine a count rate specific to each of the active sections 11 by comparing, for each scintillation photon, the irradiation position z determined with the location of the active sections 11 and summing the scintillation photons received by each of the active sections 11.

According to a third alternative embodiment illustrated in FIG. 10, the measurement probe 3 includes several identical U-shaped fibers, i.e., in particular, with identical active sections 11 in terms of location of the active section 11 along the fiber and of the length of the active section 11. The ends of each of these U-shaped fibers are connected to dedicated output connectors 23, intended to be connected to a specific photodetector 27.

According to one embodiment, the determination device 1 comprises a plurality of interchangeable measurement probes 3 forming a measurement probe kit.

The measurement probes 3 can be identical or different and, in particular, they can be designed for measurements at different body regions.

Each measurement probe 3 is provided with a chip integrating information specific to the measurement probe 3 and, in particular, calibration information specific to the measurement probe 3, for example, the calibration factor c specific to the measurement probe 3 for determining the dose as a function of the counting rate.

As an option, the chip also includes one or more of the following data specific to the measurement probe 3:

a calibration factor c specific to the measurement probe 3;

a chart of conversion factors f specific to the probe;

the parameters a and b of the calibration line f(z) for determining the irradiation position z;

the date of the last calibration of the measurement probe 3;

the date of the next calibration of the measurement probe 3 recommended by the manufacturer of the determination device 1.

This list is not exhaustive.

Each measurement probe 3 is configured so as to be detachably connected to the receiving box 55 via the additional output/input connectors 23, 25.

The chip is so configured as to communicate with the receiving box 55 when the measurement probe 3 is connected to the receiving box 55 so as to transmit to the processing module 30 the information specific to each measurement probe 3 necessary for the determination of the dose and possibly other dosimetric quantities that are to be determined.

For example, the chip is an RFID (Radio Frequency Identification) chip configured to communicate with the receiving box 55.

The disclosure also relates to a method for determining a dose deposited under the effect of irradiation by ionizing radiation during a radiological examination of a patient, by means of a determination device 1 as defined above.

In one embodiment, the method comprises:
the reception by the photodetectors 27 of the scintillation photons emitted by the active section(s) 11 under the effect of the ionizing radiation and the counting of the scintillation photons; and
the determination of the deposited dose from the measurements carried out by the photodetectors 27.

More specifically, according to an example, the determination step comprises:
computing, using the processing module 30, a counting rate corresponding to the sum of the scintillation photons counted by the photodetectors 27; and
determining the dose deposited during the irradiation in the active section 11 of measurement probe 3 by the ionizing radiation by multiplying the counting rate by the calibration factor c.

As an option, the determination step also includes:
the conversion of the measured deposited dose into a total dose received by the patient DG specific to the irradiation, for example, by multiplying the deposited dose measured by a predetermined conversion factor f or by means of an expression taking into account the dimensions of the patient as described above.

According to one embodiment, during the determination step of the DG specific to this irradiation, the processing module 30 determines, within the conversion factor chart f, the conversion factor f corresponding to the parameters of implementation of the medical imaging equipment for the irradiation considered.

As an option, the determination step also includes the determination of a specific DM for this irradiation, for example, by dividing the DG by the total length of irradiation during the radiological examination.

As an option, the determination step also includes the determination of a deposited dose per scanner revolution, a DG, and possibly a DM, per scanner revolution by applying the method described above.

As an option, the determination step includes the determination of a patient's skin dose specific to the irradiation.

The determination device 1 according to the disclosure enables a particularly accurate real-time measurement of the deposited dose.

In particular, when a straight optical probe with only one exit end is used, the signal is attenuated along the probe, and the response of the probe is not linear with the irradiation position. Thus, the measured dose may be significantly under/overestimated depending on where the irradiation takes place. To be able to display an exact dose, it would, therefore, be necessary to integrate correction factors, depending on the irradiation position. This would require prior knowledge of the irradiation position(s), which is not possible with such a straight probe. The data would have to be processed in parallel with the scanner information on the irradiation position to make cross-checks but this is very constraining, cumbersome and would make the reliability of the determination device 1 dependent on the information provided by the scanner manufacturer.

On the contrary, in the case of the U-shaped optical probe with a photodetector at each end according to the disclosure, the sum of the light signals from each channel is independent of the irradiation position because there is a compensation for the losses incurred along the fiber. In this way, the determination device 1 makes it possible to determine the deposited dose accurately and independently of the irradiation position.

In addition, the radiolucency of the measurement probes 3 makes it possible to obtain images without artefacts and, therefore, a diagnosis unbiased by our measuring system.

Compared to pencil chambers, which are currently the only measuring devices in computed tomography, the physical robustness of optical fiber-based probes makes them easier to use, without special precautions and increases their service life thanks to the reduced brittleness thereof.

The high measuring sensitivity (a factor of 1,000 for an equivalent detection volume) makes it possible to significantly reduce the size of the probes. This reduced space requirement enables use without any discomfort for the patient or the hospital staff.

Eventually, the density of the probes, equivalent to that of the tissues, enables a more accurate measurement, without the need to apply correction factors as for pencil probes, for which the interaction occurs in a gas.

In addition, the positioning system and, in particular, the positioning mat 35, enables a fast and precise positioning of the measurement probe on the scanner table 32.

In addition, the advantageously designed determination device 1 enables a real-time and patient-specific determination of the total and average doses received by the patient during an X-ray examination and, therefore, in particular, of the DPL and CTDIvoL during a computer tomographic examination.

The determination device 1 is also very versatile, since it can be easily adapted to any type of medical imaging apparatus table 32.

Eventually, the provision of a kit comprising several measurement probes 3 for a single receiving box reduces costs while enabling a wide variety of measurements to be made using a single receiving box. Storing the calibration information specific to the measurement probe at each measurement probe 3 increases safety of use by ensuring that the correct calibration information is used by the processing module 30 regardless of which measurement probe 3 is connected thereto.

The invention claimed is:

1. A radiation system, comprising:
an irradiation source configured to rotate around a patient; and
a determination device for determining a dose deposited under the effect of an irradiation with ionizing radiation generated by the irradiation source during a radiological examination of the patient, the determination device comprising:
at least one measurement probe, comprising at least one optical probe defining two exit ends, the at least one optical probe comprising at least one active section made from a scintillator and intended to emit scintillation photons under the effect of incident ionizing radiation and at least two transport sections, that are placed on either side of the active section and configured to transport the scintillation photons emitted by the at least one active section to the two exit ends;
at least one detection system comprising at least two photodetectors, each photodetector being connected to one respective exit end of the optical probe so as to receive and count the scintillation photons received from the exit end; and at least one processing module configured to determine the deposited dose on the basis of the measurements carried out by the at least two photodetectors; and wherein:

the deposited dose is directly correlated to the amount of photons emitted under the ionizing radiation received by the patient undergoing the radiological examination, the at least one processing module is configured to calculate a counting rate corresponding to a sum of the scintillation photons counted by the at least two photodetectors and to determine the dose deposited in the at least one active section of the at least one measurement probe by the ionizing radiation during the irradiation by multiplying the counting rate by a predetermined calibration factor, the determining device is further configured to convert the deposited dose into a global dose received by the patient specific to the irradiation, and the determining device is further configured to determine an average dose delivered during an acquisition covering the entire irradiation length specific to the irradiation by dividing the total dose thus determined by the total irradiation length during the radiological examination.

2. The system of claim 1, wherein the at least one optical probe is configured such that the at least one active section is exposed to ionizing radiation at the same time as the patient in order to monitor the dose deposited on each part of the patient's body in real time.

3. The system of claim 1, wherein the at least one optical probe is U-shaped.

4. The system of claim 1, wherein at least one measurement probe comprises at least two optical probes having common exit ends.

5. The system of claim 1, wherein each optical probe of the at least one measurement probe has exit ends distinct from the exit ends of any other optical probe of the at least one measurement probe, with each exit end being connected to a respective photodetector.

6. The system of claim 1, further comprising a positioning system configured for positioning the at least one measurement probe on a table of a medical imaging apparatus.

7. The determination device of claim 6, wherein the positioning system comprises a mat in which the measuring probe is disposed.

8. The system of claim 1, further comprising a receiving box housing the at least one detection system.

9. The system of claim 8, wherein the receiving box and the at least one measurement probe comprise complementary connectors configured for the releasable connection of the measurement probe to the receiving box.

10. The system of claim 9, further comprising a plurality of interchangeable measurement probes including the at least one measurement probe, each measurement probe of the plurality being provided with calibration information specific to the respective measurement probe of the plurality.

11. The system of claim 10, wherein each measurement probe of the plurality is provided with an RFID chip containing the calibration information, the RFID chip being configured to communicate the calibration information to the at least one processing module when the at least one measurement probe is connected to the receiving box.

12. The system of claim 8, wherein the receiving box is configured to be releasably attached to a table of a medical imaging apparatus, the table being movably mounted with respect to a body of the medical imaging apparatus so as to move through the irradiation field of the medical imaging apparatus.

13. The system of claim 8, further comprising a power supply system for the determining device, the power supply system comprising a rechargeable battery housed in the receiving box and a charging unit housed in a charging base and configured to recharge the battery wirelessly.

14. The system of claim 13, wherein the receiving box is configured to be releasably attached to a table of a medical imaging apparatus, the table being movably mounted with respect to a body of the medical imaging apparatus so as to move through the irradiation field of the medical imaging apparatus, and wherein the charging base comprises removable means for attachment to a stationary part of a medical imaging apparatus, the table of the medical imaging apparatus being slidably mounted with respect to the stationary part, the charging unit being configured to charge the battery when the table is in a charging position, and wherein, when the receiving box is at a distance from the charging base smaller than or equal to the maximum distance allowing the rechargeable battery to be charged, the receiving box being positioned above the charging base in the charging position.

15. The determination device of claim 13, wherein the charging unit is configured to wirelessly recharge the battery by induction.

16. The system of claim 1, wherein the at least one processing module is configured to calculate a dose deposited in the at least one active section of the at least one measurement probe per revolution of the irradiation source, corresponding to the sum of the scintillation photons counted by the at least two photodetectors during one revolution of the irradiation source.

17. The determination device of claim 1, wherein the determining device is further configured to convert the deposited dose into the global dose received by the patient specific to the irradiation by multiplying the determined deposited dose by a predetermined conversion factor.

18. The system of claim 1, further comprising a table configured to support the patient and to translate in a direction parallel to an axis of rotation of the irradiation source as the irradiation source rotates around the patient.

19. A method for determining a dose deposited under the effect of irradiation with ionizing radiation during a radiological examination of a patient, the method comprising:

providing a dose-determination device, including:

at least one measurement probe comprising at least one optical probe defining two exit ends, the at least one optical probe comprising at least one active section made from a scintillator and intended to emit scintillation photons under the effect of incident ionizing radiation and at least two transport sections, that are placed on either side of the active section and configured to transport the scintillation photons emitted by the at least one active section to the two exit ends;

at least one detection system comprising at least two photodetectors, each photodetector being connected to one respective exit end of the optical probe so as to receive and count the scintillation photons received from the exit end; and at least one processing module configured to determine the deposited dose on the basis of the measurements carried out by the at least two photodetectors; and wherein the deposited dose is directly correlated to the amount of photons emitted under the ionizing radiation received by the patient undergoing the radiological examination;

rotating an irradiation source around the patient while irradiating the patient with ionizing radiation emitted from the irradiation source;

receiving, by the at least two photodetectors, scintillation photons emitted by the at least one active section under the effect of ionizing radiation and counting the scintillation photons;

using the at least one processing module to calculate a counting rate corresponding to a sum of the scintillation photons counted by the at least two photodetectors and to determine the dose deposited in the at least one active section of the at least one measurement probe by the ionizing radiation during the irradiation by multiplying the counting rate by a predetermined calibration factor;

converting the deposited dose into a global dose received by the patient specific to the irradiation; and determining an average dose delivered during an acquisition covering the entire irradiation length specific to the irradiation by dividing the total dose thus determined by the total irradiation length during the radiological examination.

* * * * *